US008690801B2

(12) United States Patent
Nakashima et al.

(10) Patent No.: US 8,690,801 B2
(45) Date of Patent: Apr. 8, 2014

(54) LEG ASSIST DEVICE

(75) Inventors: Issei Nakashima, Toyota (JP); Shuhei Manabe, Miyoshi (JP)

(73) Assignee: Toyota Jidosha Kabushiki Kaisha, Toyota-Shi (JP)

( * ) Notice: Subject to any disclaimer, the term of this patent is extended or adjusted under 35 U.S.C. 154(b) by 0 days.

(21) Appl. No.: 13/611,659

(22) Filed: Sep. 12, 2012

(65) Prior Publication Data

US 2013/0006159 A1 Jan. 3, 2013

Related U.S. Application Data

(63) Continuation of application No. PCT/JP2010/060455, filed on Jun. 21, 2010.

(51) Int. Cl.
*A61B 5/22* (2006.01)

(52) U.S. Cl.
USPC .................................................. 601/5; 601/35

(58) Field of Classification Search
USPC .......................... 601/35, 5, 23, 24, 25, 33, 34
See application file for complete search history.

(56) References Cited

U.S. PATENT DOCUMENTS

| | | | | |
|---|---|---|---|---|
| 8,181,520 | B2 * | 5/2012 | Kadota et al. | 73/379.01 |
| 2004/0158175 | A1 * | 8/2004 | Ikeuchi et al. | 601/5 |
| 2004/0167641 | A1 | 8/2004 | Kawai et al. | |
| 2006/0270951 | A1 | 11/2006 | Ikeuchi | |
| 2008/0156363 | A1 | 7/2008 | Ikeuchi et al. | |
| 2008/0234608 | A1 * | 9/2008 | Sankai | 601/5 |
| 2008/0289670 | A1 | 11/2008 | Ashihara et al. | |
| 2008/0312049 | A1 | 12/2008 | Ido et al. | |
| 2008/0318739 | A1 | 12/2008 | Ashihara et al. | |
| 2009/0014042 | A1 | 1/2009 | Ashihara et al. | |
| 2009/0048686 | A1 | 2/2009 | Ikeuchi et al. | |
| 2009/0170662 | A1 | 7/2009 | Ido | |
| 2009/0199883 | A1 | 8/2009 | Hiki | |
| 2010/0271051 | A1 | 10/2010 | Sankai et al. | |
| 2011/0306907 | A1 * | 12/2011 | Ashihara et al. | 601/35 |

FOREIGN PATENT DOCUMENTS

| | | |
|---|---|---|
| JP | 2003-079684 A | 3/2003 |
| JP | 2004-121569 A | 4/2004 |
| JP | 2005-224558 A | 8/2005 |

(Continued)

OTHER PUBLICATIONS

International Search Report and Written Opinion of PCT/JP2010/060455 mailed Oct. 5, 2010.

*Primary Examiner* — Steven Douglas
(74) *Attorney, Agent, or Firm* — Kenyon & Kenyon LLP

(57) ABSTRACT

A leg assist device with a control law suitable for assisting standing up motion is provided. The leg assist device is provided with an upper leg link, a lower leg link, a rotary joint, and a controller. The upper leg link and the lower leg link is attached to a leg of a user. The rotary joint rotatably connects the lower leg link to the upper leg link. The rotary joint also has an actuator which rotates the lower leg link. The controller controls the actuator so that the lower leg link angle matches a target angle. The controller has a torque limiter that limits the magnitude of the command torque that is output to the actuator. The controller sets a standing position angle corresponding to a user's standing position to the target angle, and raises an upper limit of the torque limiter as a user's hip height rises.

4 Claims, 7 Drawing Sheets

(56) References Cited

FOREIGN PATENT DOCUMENTS

| | | | |
|---|---|---|---|
| JP | 2008-006076 | A | 1/2008 |
| JP | 2008-067849 | A | 3/2008 |
| JP | 2008-068046 | A | 3/2008 |
| JP | 2008-086586 | A | 4/2008 |
| JP | 2009-060946 | A | 3/2009 |
| JP | 2009-172117 | A | 8/2009 |
| JP | 2009-207840 | A | 9/2009 |
| JP | 2010-119499 | A | 6/2010 |
| WO | 2006/129599 | A1 | 12/2006 |
| WO | 2009084387 | A1 | 7/2009 |

* cited by examiner

LEG ASSIST DEVICE

TECHNICAL FIELD

This is a Continuation of International Application No. PCT/JP2010/060455 filed Jun. 21, 2010, the disclosure of which is hereby incorporated by reference herein in its entirety. The present invention relates to a leg assist device that assists standing up motion of a user. Especially, the invention relates to a leg assist device that assists standing up motion of a user by applying torque to a knee joint.

BACKGROUND ART

An assist device that assists user's motion by applying torque to joints has been developed. Among such assist devices, a device that reinforces muscle power for a healthy person may be commonly called a "powered exoskeleton". A device that assists muscle power for a user whose muscle power has declined or a user who has difficulty to move joints on his/her own may be commonly called as a "motion assist device". With regards to the motion assist device, great numbers of researches on assisting leg muscle power, especially walking motion, are being made. A device that assists the leg muscle power is referred to as a "leg assist device" herein.

The leg assist device mainly assists the muscle for moving a knee joint. Such device typically has a mechanical configuration in which an upper leg link to be attached to the user's upper leg and a lower leg link to be attached to the user's lower leg are connected. The upper leg link and the lower leg link are connected by a rotary joint with an actuator. The device guides swing of the user's lower leg, i.e., knee joint motion, by driving the lower leg link. One example of the leg assist device having the above mechanical configuration is disclosed in Japan patent application publication No. 2008-006076.

The leg assist device having the above mechanical configuration can assist walking motion, standing up motion, and seating motion by changing a control law for the actuator. The technique disclosed herein provides a leg assist device with a control law for assisting standing up motion. One example of the device assisting standing up motion is disclosed in Japan patent application publication No. 2009-060946.

SUMMARY ON THE INVENTION

In general, there are two types of control for an actuator that moves a link of a robot: angle control (position control) and torque control (power control). In the angle control, an angle of the link is given as a target value. In the torque control, torque to be output by the link is given as a target value. A controller controls the actuator so that the angle of the link or the output torque matches the given target value. In case of the angle control, the angle of the link matches the target angle. In this case, the output torque of the actuator varies depending on the load applied to the link (joint). In case of the torque control, the output torque of the joint (actuator) matches the target torque. In this case, the angle of the link is determined by the balance between the target torque (output torque) and the load. That is, the angle of the link varies depending on the load. Thus, in the angle control, although the angle of the link can be determined, the output torque becomes indeterminate. Conversely, in the torque control, although the output torque of the link can be determined, the angle of the link becomes indeterminate. Meanwhile, in the technical field of robots, compliance control is known in which rigidity is given, together with the angle of the link, as the target value. In the case of the compliance control, "rigidity" corresponds to a parameter determining the relationship between the link angle and link output torque to be realized. In case the compliance control has been employed, deviance from the target angle and torque to be output by the link are determined depending on the load applied to the link. That is, the controller employing the compliance control adjusts the angle of the link so that the relationship between difference and output torque satisfies a relationship determined by a specific "rigidity".

In the case of the assist device that assists the standing up motion, each of the angle control, the torque control and the compliance control has disadvantages in being the control for the actuator that rotates the lower leg link. In the case of the angle control, the controller rotates the lower leg link according to a predetermined target trajectory. Consequently, in case the angle control has been employed, the leg assist device starts to rotate the lower leg link regardless of the condition of the user. Note that, the "target trajectory" means time-series data of the target angle (or target torque). In the case of the torque control and the compliance control, as described above, the lower leg link angle is not determined. The present specification teaches a leg assist device with a control law suitable for assisting the standing up motion.

The technique taught in the present specification presents a leg assist device that reinforces muscle power of a leg when a user stands up. As described above, the mechanical configuration of the leg assist device comprises an upper leg link, a lower leg link, a rotary joint and a controller. The upper leg link is attached to an upper leg of the user, and the lower leg link is attached to a lower leg of the user. The rotary joint rotatably connects the lower leg link to the upper leg link. Further, the rotary joint has an actuator that rotates the lower leg link. The controller has a feed-back control module that computes a command torque for the actuator based on a difference between a lower leg link angle and a target angle, and the controller controls the actuator so that the lower leg link angle matches the target angle. As one feature of the novel leg assist device taught in the present description, the controller further has a torque limiter that limits magnitude of the command torque. The torque limiter limits the input command torque to equal to or below an upper limit torque. The controller sets the target angle to a standing position angle corresponding to the user's standing position, and raises an upper limit (upper limit torque) of the torque limiter while the hip height of the user rises.

The leg assist device has the feed-back control module that controls the actuator so that the difference between the lower leg link angle and the target angle is small, and basically controls the lower leg link angle by angle control. The target angle is set to a lower leg link angle (standing position angle) corresponding to a standing position. The standing position angle is essentially equivalent to the lower leg link angle when the upper leg link and the lower leg link are aligned along a straight line. Furthermore, below, the actual rotary angle of the lower leg link may be called a measured angle.

The leg assist device essentially employs the angle control, but the torque output by the actuator is limited by the torque limiter. The controller raises the upper limit torque as the user's hip height rises. Even if there is a large difference between the target angle and the measured angle, the output torque is limited by the upper limit torque while the hip height is low.

The upper limit torque while the hip height is low is set to magnitude insufficient to support the weight of the user. Consequently, while the hip height is low, the user cannot raise the hip without exerting his/her muscle power. Consequently, while the hip height is low, the leg assist device does not begin to move spontaneously. That is, the user can take the initiative for the standing up motion when starting the standing up motion and for a short period thereafter.

The upper limit torque increases as the hip height rises. Consequently, the output torque of the leg assist device becomes proportional to the difference. That is, the angle control takes the initiative for the standing up motion as the hip height rises. Consequently, the leg assist device reliably leads the user to a standing position. Thus, the leg assist device taught in present specification gives the initiative for the standing up motion to the user at the beginning. Then, when the hip height rises, the leg assist device takes the initiative for motion and reliably guides the user to the standing position.

By changing the upper limit torque depending on the hip height, the controller functions in effect as torque control when the hip height is low, and smoothly switches to the angle control as the hip height rises. This leg assist device realizes a control law that switches smoothly from the torque control to the angle control depending on the hip height. According to this control law, the leg assist device can allow the user to determine the timing to start standing up, and can reliably guide the user to the standing position.

The hip height corresponds to a knee joint angle. Consequently, the leg assist device may actually employ, as the sensor that measures the hip height, an angle sensor that measures the knee joint angle (rotary angle of the lower leg link). Here, the knee joint angle is defined as an angle formed by the upper leg and the lower leg at the inner side of the knee. According to this type of definition, the knee joint angle grows larger as the standing up proceeds. According to this type of definition, “raising the upper limit of the torque limiter as the user’s hip height rises” may be equivalent to “raising the upper limit of the torque limiter as the knee joint angle grows larger”.

Further, the hip height also relates to a tilt angle around the pitch axis of the user’s upper leg relative to the vertical direction. Consequently, the leg assist device may also actually employ, as the sensor that measures the hip height, a sensor that measures the tilt angle around the pitch axis of the upper leg relative to the vertical direction. Thus, in other words, “raising the upper limit of the torque limiter as the user’s hip height rises” may be equivalent to “raising the upper limit of the torque limiter while the tilt angle around the pitch axis of the upper leg relative to the vertical direction grows smaller”.

Of course, the leg assist device may employ, as the sensor that measures the hip height, a distance sensor that measures the distance between the hip and a bed (or a seating surface of a chair).

The control law of the leg assist device of the present specification is substantially equivalent to the torque control when the hip height is low, and is essentially equivalent to the angle control when the hip height is high. The control law of the leg assist device smoothly switches from the torque control to the angle control as the hip rises. The leg assist device that has adopted this type of control law can smoothly assist the standing up motion of the user.

DESCRIPTION OF EMBODIMENTS

Preferred Aspects of Invention

Several technical features of a leg assist device 10 of the embodiment will be noted.

(Feature 1) In case a hip height does not reach a predetermined threshold height within a predetermined time period from starting standing up assist control, a controller 30 changes a target angle to a seated position angle corresponding to a seated position of a user. Alternatively, in case the hip height does not reach the predetermined threshold height within the predetermined time period from starting standing up assist control, the controller 30 raises an upper limit of a torque limiter. The former “predetermined time period” and the latter “predetermined time period” may be the same, or may differ. Similarly, the former “predetermined threshold height” and the latter “predetermined threshold height” may be the same, or may differ.

The former process corresponds to a process smoothly halting the standing up motion in case the hip is not raised to the predetermined height within the predetermined time period. The latter process corresponds to a process gradually increasing output torque in case the hip is not raised to the predetermined height within the predetermined time period.

The former process and the latter process may also be combined. In that case, it is preferred that a controller 30 is configured so that, in case the hip height does not reach a predetermined first threshold height within a first predetermined time period from starting the standing up assist control, the controller 30 raises the upper limit of the torque limiter and, in case the hip height does not reach a predetermined second threshold height within a second predetermined time period that is longer than the first predetermined time period, the controller 30 changes the target angle to the seated position angle that corresponds to the user’s seated position. The first threshold height may be identical to or may differ from the second threshold height. The first threshold height and the second threshold height may be a hip height corresponding to the standing position.

(Feature 2) The controller 30 vibrates a lower leg link 50 before changing the target angle to the seated position angle. The vibration of the lower leg link 50 performs the role of informing the user of the change in the target angle.

Embodiments

Figure 1:
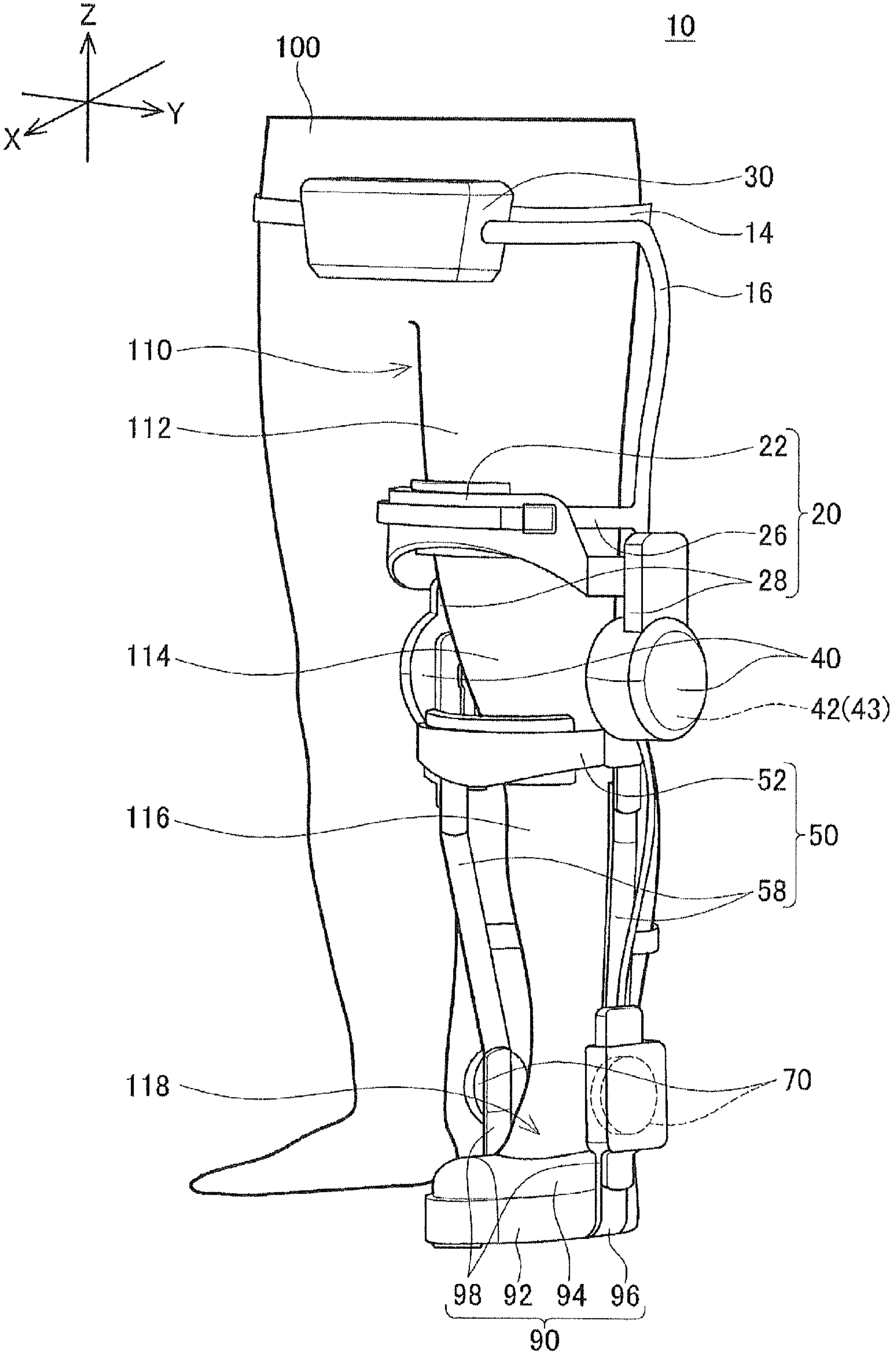
FIG. 1 shows a schematic perspective view of a leg assist device.

An embodiment of the present invention will be described with reference to the figures. FIG. 1 is an external view of a leg assist device 10 of the embodiment. As shown in FIG. 1, the leg assist device 10 is attached to a leg of a user 100. In this embodiment, the leg assist device 10 is attached to a left leg of the user 100. The leg assist device 10 comprises a motor 42 that applies torque to a left knee joint of the user, as will be described. By changing a control law of the motor, this leg assist device 10 can assist a walking motion, a standing up motion, and a seating motion. The leg assist device 10 is used, for example, in rehabilitation of the user 100 who cannot voluntarily move the knee joint of one leg. Using the leg assist device 10, it can promote functional recovery of the user 100 and can reduce burden of an assistant who assists the user 100.

The description of the present embodiment focuses on assisting the standing up motion. However, it should be noted that, by changing the control law, the leg assist device 10 can also be used to assist the walking motion.

A coordinate system used in the description of the present embodiment will be described. A front-back direction of the user 100 to whom the leg assist device 10 is attached is determined as an X axis, a left-right direction of the user 100 is determined as a Y axis, and an up-down direction of the user 100 is determined as a Z axis. Furthermore, a forward direction of the X axis is determined as the front of the user 100, a forward direction of the Y axis is determined as the left of the user 100, and a forward direction of the Z axis is determined as the upper direction of the user 100. Furthermore, in the field of robotics, the X axis, Y axis and Z axis in the coordinate system fixed to the robot (human body in the present embodiment) are respectively called a roll axis, pitch axis and yaw axis.

The mechanical configuration of the leg assist device 10 will be described. As shown in FIG. 1, the leg assist device 10 comprises a controller 30, an upper leg link 20, a lower leg link 50 and a foot link 90. The controller 30 contains a CPU for controlling the motor 42 (to be described), and a battery. The controller 30 supplies power to the parts of the leg assist device 10, and controls the motion of the parts of the leg assist device 10. The controller 30 is attached, for example, to a trunk (waist) of the user 100. The controller 30 comprises an attachment belt 14 for fixing the controller 30 to the trunk of the user 100. Furthermore, there is no particular restriction on the position of attaching the controller 30, and the controller 30 may for example be attached to a back of the user 100.

The upper leg link 20, the lower leg link 50 and the foot link 90 are attached to an affected leg 110 (leg requiring assistance: here the left leg) of the user 100. In detail, the upper leg link 20 is attached to an upper leg 112, the lower leg link 50 is attached to a lower leg 116, and the foot link 90 is attached to a foot 118. Furthermore, in the present specification, in case the expression "the affected leg 110" alone is used, this includes not just the upper leg 112, knee 114 and the lower leg 116, but also the foot 118 (the portion at the distal side from the ankle).

The upper leg link 20 has an upper leg support plate 22, an upper leg belt 26 and frames 28. The upper leg support plate 22 is fixed to a pair of the frames 28. The upper leg support plate 22 makes contact with a front surface of the upper leg 112 of the user 100. The upper leg support plate 22 is formed, for example, from fiber-reinforced plastic. The upper leg support plate 22 may be formed from metal material. There is no particular restriction on the material of the upper leg support plate 22, as long as it is strong enough to support the user.

The lower leg link 50 has a lower leg support plate 52 and frames 58. The lower leg support plate 52 is fixed to a pair of the frames 58. The lower leg support plate 52 makes contact with a front surface (below the knee) of the lower leg 116 of the user 100. The lower leg support plate 52 is formed, for example, from fiber-reinforced plastic. Furthermore, as with the upper leg support plate 22, the lower leg support plate 52 may be formed from another material having the necessary rigidity.

Next, the foot link 90 will be described. As shown in FIG. 1, the foot link 90 has frames 98, a foot support plate 92 and a shoe 94. The foot support plate 92 is fixed to a pair of the frames 98. The foot support plate 92 is disposed below the foot 118 (at a base of the foot) of the user 100. The foot support plate 92 is formed, for example, from fiber-reinforced plastic, and has comparatively high rigidity. Furthermore, as with the upper leg support plate 22 and the lower leg support plate 52, the foot support plate 92 may be formed from another material having the necessary rigidity.

The shoe 94 is formed on an upper surface (the surface facing the foot 118) of the foot support plate 92. The shoe 94 has the same features as a normal shoe. The shoe 94 is attached removably to the foot support plate 92, allowing it to be changed in response to the size and shape of the foot 118 of the user 100. The shoe 94 is fixed to the foot support plate 92 by, for example, a surface fastener. A load sensor 96, which detects load exerted on the foot sole of the affected leg, is embedded in the foot support plate 92. Load data measured by the load sensor 96 is sent to the controller 30.

The upper leg link 20 and the lower leg link 50 are connected via a pair of rotary joints 40. Each of the pair of rotary joints 40 is a rotary joint that performs uniaxial rotation about the pitch axis (Y axis), and rotatably connects the frame 28 of the upper leg link 20 and the frame 58 of the lower leg link 50. That is, the rotary joint 40 rotatably connects the lower leg link 50 to the upper leg link 20. Furthermore, the fixing position of the frames 28 of the upper leg link 20 and the fixing position of the frames 58 of the lower leg link 50 can be adjusted according to the body shape of the user, 100.

The motor 42, an angle sensor (encoder) 43, and a reducer are contained in the rotary joint 40 positioned at the outer side of the affected leg 110. This rotary joint corresponds to a drive unit that rotates the lower leg link 50 relative to the upper leg link 20. This rotary joint 40 is connected to the controller 30 via an electric cable 16, is driven by power supplied from the controller 30, and the motion of the rotary joint 40 is controlled by the controller 30. The control of the lower leg link 50 will be described later.

The angle sensor 43 measures a rotary angle of the lower leg link 50. The rotary angle of the lower leg link 50 corresponds to the knee joint angle of the user 100. As will be described, in the present embodiment the rotary angle of the lower leg link 50 (the knee joint angle) is defined as an angle between the upper leg and the lower leg at the knee inner side.

The lower leg link 50 and the foot link 90 are connected via a pair of ankle rotary joints 70. Each of the pair of ankle rotary joints 70 is a rotary mechanism that performs uniaxial rotation about the pitch axis, and rotatably connects the frame 98 of the foot link 90 to the frame 58 of the lower leg link 50. The positions where the foot link 90 is fixed to the ankle rotary joints 70 can be adjusted according to the body shape of the user 100.

As described above, the leg assist device 10 is attached to the leg of the user, and assists the motion of the lower leg 116 by applying torque to the knee joint. Below, the controls will be described when the leg assist device 10 assists the standing up motion of the user.

Figure 2:
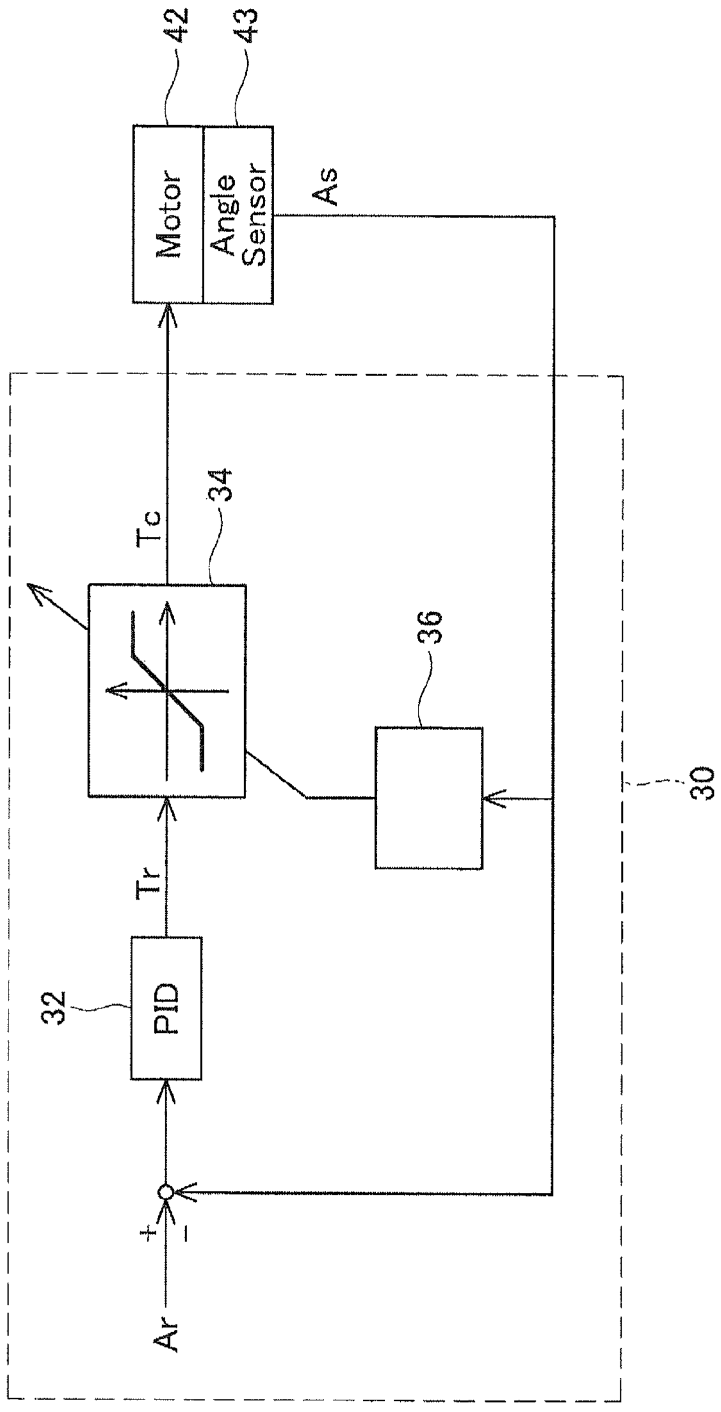
FIG. 2 shows a block diagram of a control system of the leg assist device.

FIG. 2 shows a block view of a control system (the controller 30) of the leg assist device 10. The controller 30 comprises a feed-back control module 32, a torque limiter 34 and a torque adjusting module 36. The controller 30 controls the motor 42 so that a rotary angle As of the lower leg link 50 matches a target angle Ar. In detail, the feed-back control module 32 of the controller 30 computes target torque Tr by multiplying the gain with the difference between the target angle Ar of the lower leg link 50 and the rotary angle As of the lower leg link 50. Furthermore, the rotary angle As is measured by the angle sensor 43. A PID control law is implemented in the feed-back control module 32, and the target torque Tr in response to the difference (Ar−As) is output. Since the PID control law is well-known, a description of its specific structure is omitted. The feed-back control module 32 may use a control law other than PID, such as an H-infinity control law.

The target torque Tr is input to the torque limiter 34. The torque limiter 34 limits the target torque Tr to equal or below a given upper limit torque Tmax. The output of the torque limiter 34 corresponds to a command torque Tc to the motor 42. The motor 42 outputs torque having the magnitude equivalent to the command torque Tc.

The "target torque" also corresponds to the command torque output to the motor 42 (actuator). As will be described, the controller 30 outputs the command torque limited by the torque limiter to the motor 42. In order to distinguish the "command torque" limited by the torque limiter, the command torque prior to being input to the torque limiter is called "target torque".

Figure 3A:
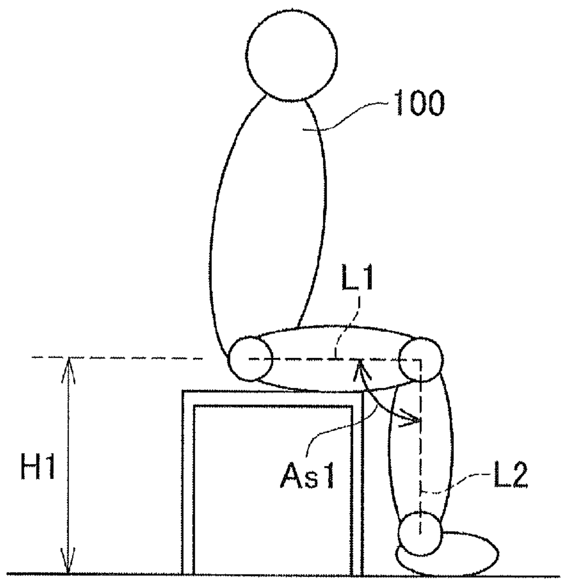
FIG. 3A is a view showing a seated position.
Figure 3B:
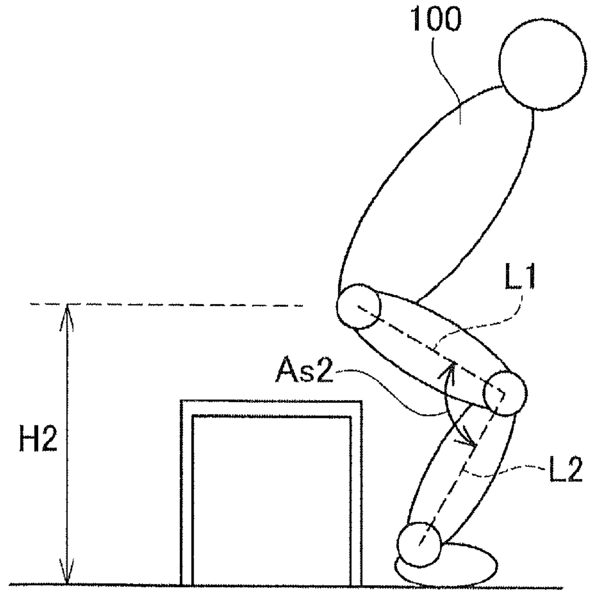
FIG. 3B is a view showing position while standing up.
Figure 3C:
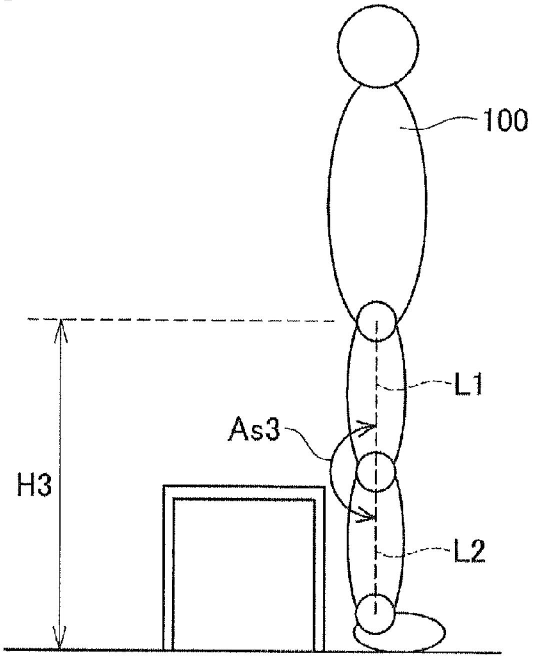
FIG. 3C is a view showing a standing position.

The upper limit torque Tmax is changed by the torque adjusting module 36 in response to the rotary angle As of the lower leg link 50. Furthermore, the rotary angle As corresponds to the user's hip height H. This is described using FIG. 3A-FIG. 3C. FIG. 3A schematically shows a seated position. FIG. 3C schematically shows a standing position. FIG. 3B schematically shows a position during standing up. In FIGS. 3A-3C, a straight line L1 shows a center line of the upper leg, and a straight line L2 shows a center line of the lower leg. The center line L1 of the upper leg is a straight line extending along the longitudinal direction of the upper leg, and the center line L2 of the lower leg is a straight line extending along the longitudinal direction of the lower leg. The rotary angle As of the lower leg link 50 is equivalent to the knee joint angle of the user. The knee joint angle of the user, i.e., the rotary angle As of the lower leg link 50, is defined as the angle between the upper leg link and the lower leg link at the inner side of the knee. In more detail, the rotary angle As is defined as the angle between the center line L1 of the upper leg and the center line L2 of the lower leg at the inner side of the knee. As shown in FIG. 3A, a rotary angle As1 in the seated position is approximately 90 degrees. As shown in FIG. 3C, a rotary angle As3 in the standing position is approximately 180 degrees. A rotary angle As2 during standing up is between 90 degrees (As1) and 180 degrees (As3). The rotary angle As1 corresponding to the seated position is called a seated position angle, and the rotary angle As3 corresponding to the standing position is called a standing position angle.

In FIGS. 3A-3C, the letter H indicates the hip height. In the standing up motion, the knee joint angle (i.e., the rotary angle As of the lower leg link 50) increases monotonically together with the increase in the hip height H. Consequently, in the standing up motion, the hip height H corresponds uniquely to the rotary angle As. That is, the seated position angle As1 corresponds to a hip height H1 while in the seated position, and the standing position angle As3 corresponds to a hip height H3 while in the standing position. Further, the rotary angle As2 corresponds to a hip height H2 during standing up. Thus, when the standing up motion is assisted, the angle of the lower leg link 50 represents the hip height.

Figure 4:
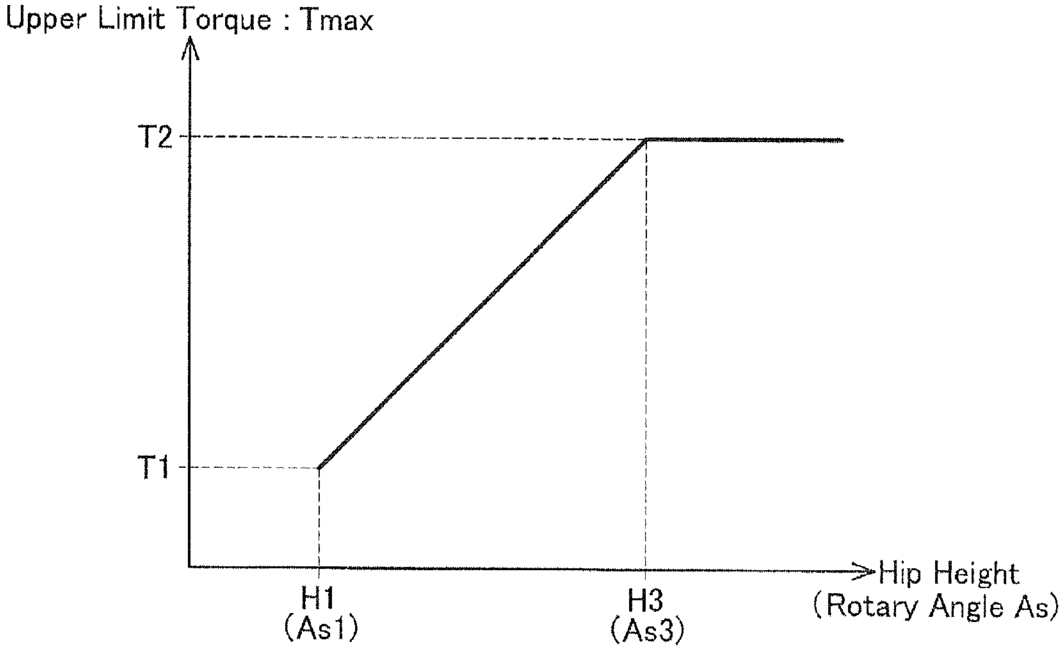
FIG. 4 is a graph showing specifics of a torque limiter.

The torque adjusting module 36 of the controller 30 changes the upper limit torque Tmax in the torque limiter 34 depending on the hip height H (i.e., the rotary angle As of the lower leg link 50). Specifically, as the hip height H rises (as the rotary angle As of the lower leg link 50 increases), the torque adjusting module 36 raises the upper limit torque Tmax. FIG. 4 shows an example of change to the upper limit torque Tmax. At the hip height H1 equivalent to the seated position (equivalent to the seated position angle As1), the upper limit torque Tmax is T1, and at the hip height H3 equivalent to the standing position (equivalent to the standing position angle As3), the upper limit torque Tmax is T2. The upper limit torque Tmax increases monotonically from T1 to T2 as the hip height H increases. Here, the upper limit torque T1 is set to magnitude insufficient to support the user's weight. The torque adjusting module 36 changes the upper limit torque Tmax in the torque limiter 34 based on the relationship in the graph of FIG. 4. The torque limiter 34 limits the target torque Tr to the upper limit torque Tmax. That is, FIG. 4 defines the motion characteristics of the torque limiter 34. The torque that has been limited corresponds to the command torque Tc output to the motor 42.

The advantages of the torque limiter 34 (and the torque adjusting module 36) will be described. While the hip height H is low, the output torque of the motor 42 is limited by the upper limit torque Tmax (=T1) even if the difference between the target angle Ar and the angle As increases. Since constant torque is output while the hip height is low regardless of the difference (Ar−As), the controller 30 essentially controls the motor 42 based on a torque control law during this period.

The upper limit torque T1 while the hip height is low is set to a value so small as to be insufficient to support the user's weight. Consequently, while the hip height is low, raising of the hip cannot be started without the user exerting his/her muscle power. That is, the user can take the initiative for the standing up motion when starting the standing up motion and for a short period thereafter. The start of the standing up motion is not determined spontaneously by the leg assist device 10, but can be determined by the user.

The upper limit torque Tmax increases as the hip height rises. Consequently, the output torque of the leg assist device 10 becomes proportional to the difference (Ar−As). That is, angle control becomes dominant as the hip height rises. The angle control takes initiative for the standing up motion as the hip height rises. Consequently, the leg assist device 10 reliably leads the user to the standing position. Thus, when starting, the leg assist device 10 essentially assists the user's lower leg based on the torque control, giving the user the initiative for the standing up motion. Then, as the hip height rises, the angle control becomes dominant and the leg assist device 10 takes the initiative in the standing up motion, guiding the user reliably to the standing position.

Figure 5:
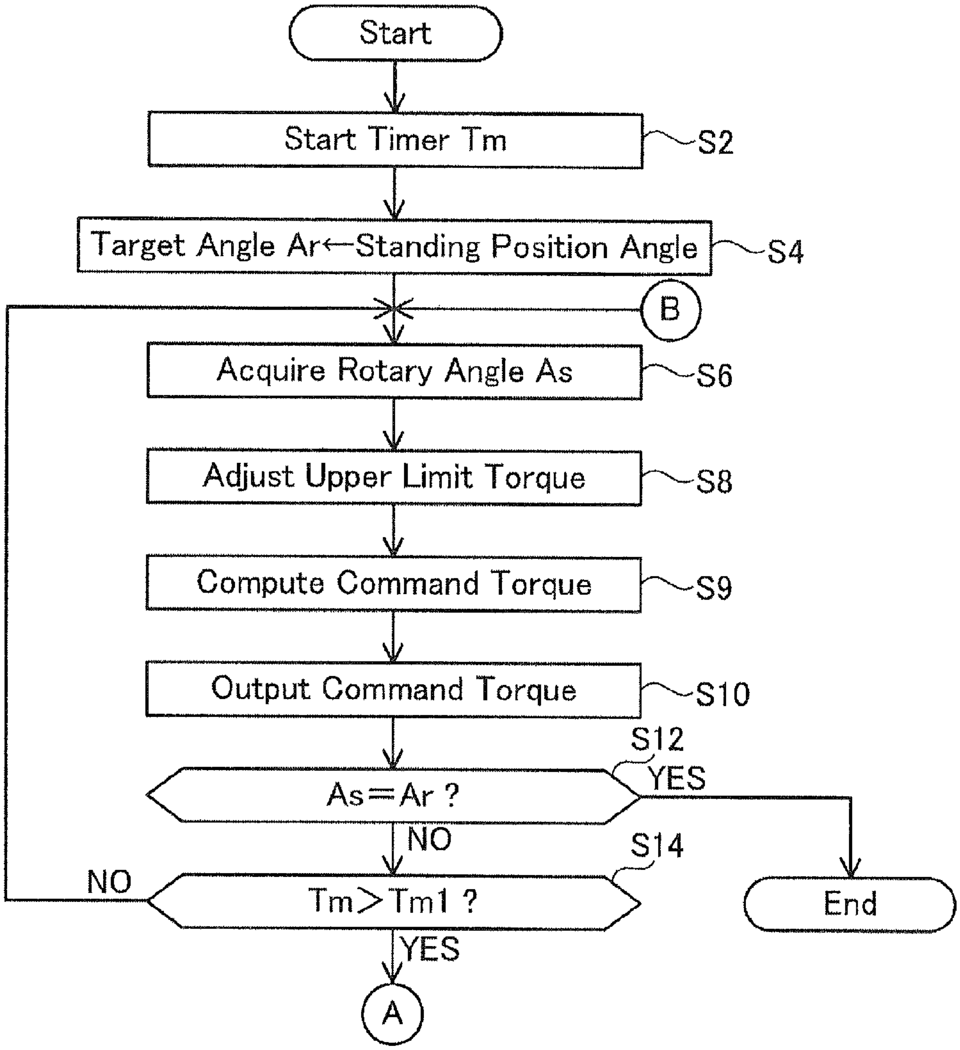
FIG. 5 is a flowchart of the control system.
Figure 6:
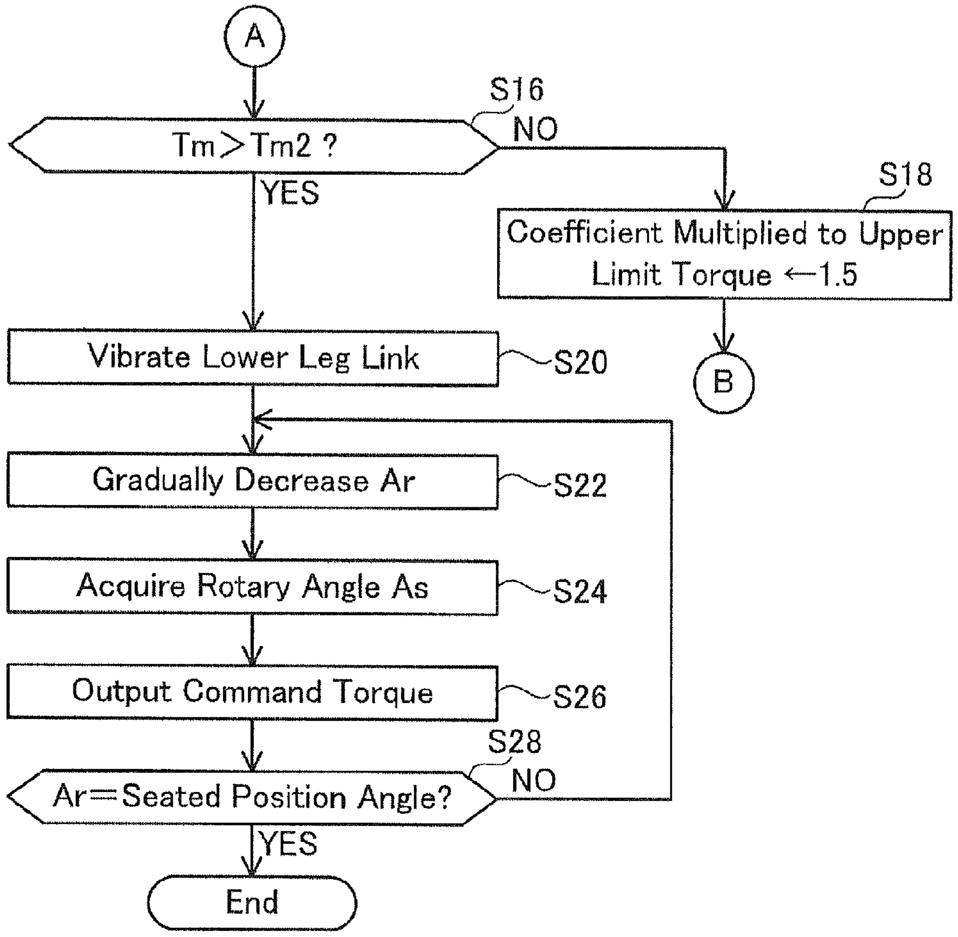
FIG. 6 is the flowchart of the control system (continued).

The processes executed by the controller 30 are described in detail in the flowchart of FIG. 5 and FIG. 6. When the control is started, the controller 30 first starts a timer (S2). The elapsed time measured by the timer is represented by the letters Tm. Tm indicates the time elapsed since starting the standing up assist control. Next, the controller 30 sets an angle of the lower leg link 50 corresponding to the standing position (the standing position angle As3) as the target angle Ar (S4). As shown in FIG. 3C, the standing position angle corresponds to the rotary angle of the lower leg link 50 when the user is in the standing position, and is approximately 180 degrees.

Next, the controller 30 acquires the rotary angle As of the lower leg link 50 using the angle sensor 43 (S6). Based on the relationship of the graph shown in FIG. 4, the controller 30 adjusts the upper limit torque Tmax depending on the angle As (S8). The controller 30 applies the PID control law to the difference between the target angle Ar and the rotary angle As, thus computing the target torque Tr (S9). Here, the controller 30 (the torque limiter 34) limits the target torque Tr to the upper limit torque Tmax. The limited target torque corresponds to the command torque Tc. The controller 30 outputs the command torque Tc, which has been limited to the upper limit torque Tmax, to the actuator 42 (S10). The motor 42 outputs a torque corresponding to the command torque Tc. The output torque is applied to the knee joint, and assists the standing up motion of the user.

The controller 30 repeats the processes of steps S6 to S10 until the rotary angle As matches the target angle Ar. When the rotary angle As matches the target angle Ar (the standing position angle As3), the control is ended (S12: YES). Furthermore, as described above, it should be noted that the upper limit torque Tmax increases as the rotary angle As increases (as the hip height rises).

The processes of steps S6 to S12 are repeated while the elapsed time Tm from starting control for assisting the standing up motion has not reached a first predetermined time period Tm1 (S14: NO). In case the rotary angle As has not reached the target angle Ar (S14: YES) even if the elapsed time Tm exceeds the first predetermined time period Tm1, the process moves to step S16 (see FIG. 6).

In step S16, the controller 30 checks whether the elapsed time Tm exceeds a second predetermined time period Tm2. In case the second predetermined time period Tm2 has not been exceeded, 1.5 is substituted for the coefficient by which the upper limit torque is multiplied (S18). Then the process returns to step S6. The "coefficient by which the upper limit torque is multiplied" is a coefficient further multiplied by the upper limit torque Tmax adjusted in step S8. When step S16 is executed, the upper limit torque Tmax computed in step S8 becomes 1.5 times greater. That is, in case the hip height does not reach the predetermined threshold height within the predetermined time period Tm1 from starting the standing up assist control, the controller 30 raises the upper limit of the torque limiter. The controller 30 increases the torque applied to the user by this process in case the hip is not raised even after a certain period has elapsed. Since the torque applied to the user increases, the assistance in standing up is enhanced.

The second predetermined time period Tm2 is set to be a period longer than the first predetermined time period Tm1. In case the elapsed time Tm exceeds the second predetermined time period Tm2 (S16: YES), the controller 30 controls the motor 42 to vibrate the lower leg link 50 for a brief time (S20). Next, the controller 30 decreases the target angle Ar to the rotary angle As (the seated position angle As1) which corresponds to the seated position (S22, S28). That is, in case the hip height does not reach the predetermined threshold height within the second predetermined time period Tm2 from starting the standing up assist control, the controller 30 changes the target angle Ar to the seated position angle As1. While reducing the target angle Ar, the controller 30 acquires the rotary angle As (S24), and outputs the command torque Tc based on the difference between the acquired rotary angle As and the target angle Ar (S26). That is, the controller 30 outputs the command torque Tc that depends on the changing target angle Ar (S26).

The process from step S22 to S28 correspond to a process of smoothly ending the standing up motion in the case where the standing up motion has not started even if the second predetermined time period Tm2 has been exceeded. By reducing the target angle Ar from the standing position angle As3 to the seated position angle As1, the torque output by the motor 42 is reduced. Eventually, the output torque in the seated position becomes zero.

The controller 30 vibrates the lower leg link 50 before changing the target angle Ar to the seated position angle As1 (S20). This process provides the advantage of informing the user the change in the target angle Ar.

Figure 7:
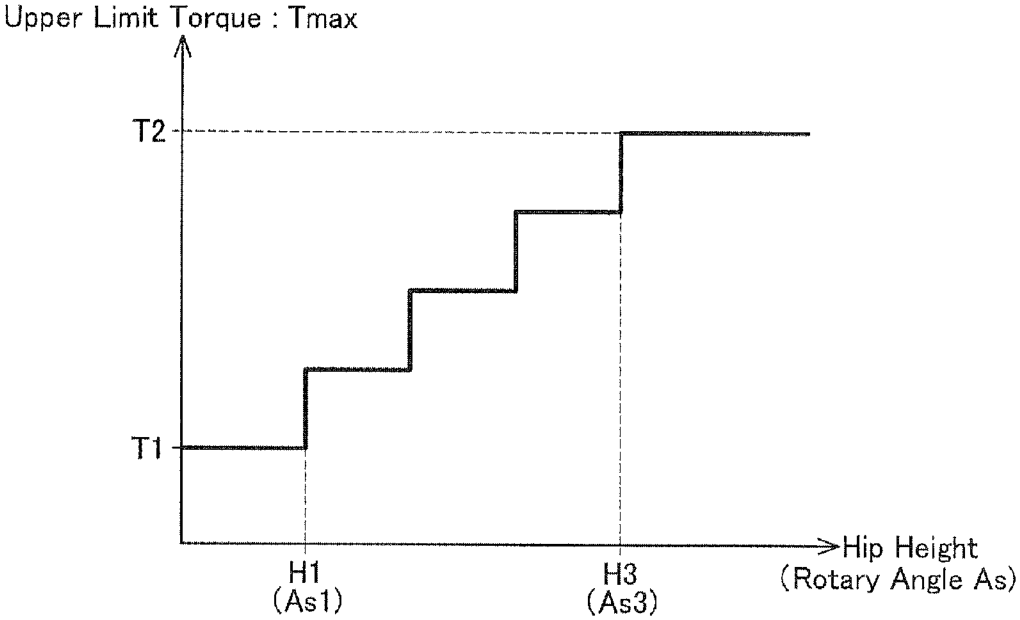
FIG. 7 is a graph showing specifics of another torque limiter.
Figure 8:
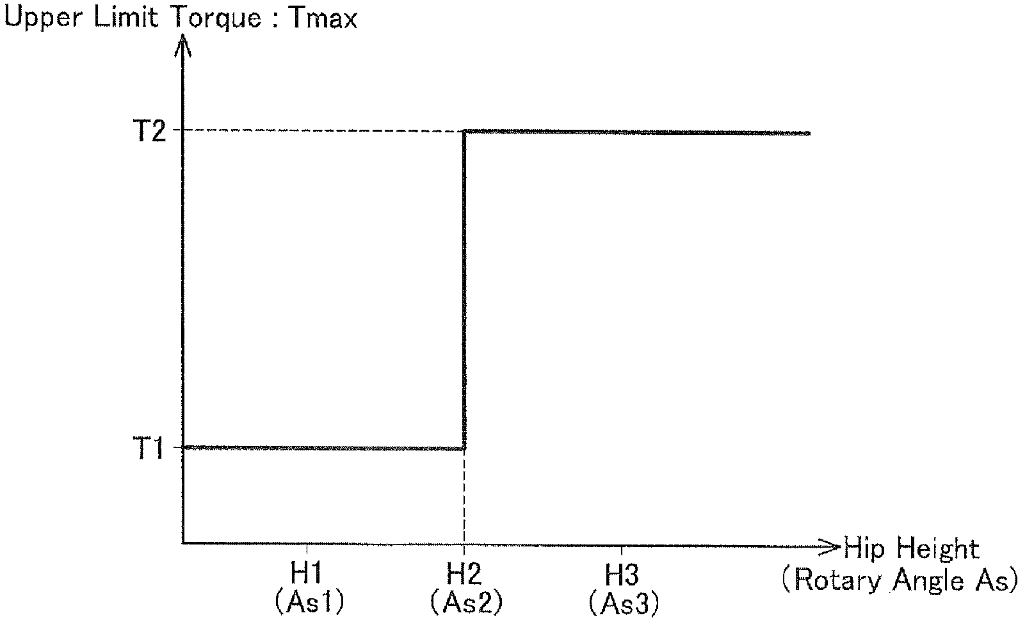
FIG. 8 is a graph showing specifics of yet another torque limiter.

A preferred embodiment of the present invention was described above. Preferred modifications of the leg assist device 10 of the embodiment will be described. The controller 30 may change the upper limit torque in a manner other than the graph shown in FIG. 4. Other examples of graph of the upper limit torque Tmax are shown in FIG. 7 and FIG. 8. The controller 30 may change the upper limit torque according to the graph of FIG. 7 or the graph of FIG. 8. The graph of FIG. 7 shows an example in which the upper limit torque Tmax is raised by step levels as the hip height rises. The graph of FIG. 8 shows the upper limit torque Tmax being set to T1 in case of being lower than the intermediate hip height H2 positioned between the seated position hip height H1 and the standing position hip height H3, and the upper limit torque Tmax being set to T2 in case of being higher than the intermediate hip height H2. In the case of the graph of FIG. 8, the controller 30 sets the upper limit torque Tmax to T1 in case of being lower than the intermediate hip height H2, which is positioned between the seated position hip height H1 and the standing position hip height H3, and sets the upper limit torque Tmax to T2 in case of being higher than the intermediate hip height H2. In other words, the controller 30 sets the upper limit torque Tmax to T1 in case the rotary angle As of the lower leg link 50 is lower than the intermediate angle As2 which is positioned between the seated position angle As1 equivalent to the seated position and the standing position angle As3 equivalent to the standing position, and sets the upper limit torque Tmax to T2 in case the angle As of the lower leg link 50 is higher than the intermediate hip height H2. The torque T2 is greater than T1.

In the leg assist device 10 of the embodiment, an angle sensor that measures the angle of the lower leg link 50 was used to measure (estimate) the hip height. The hip height also corresponds uniquely to the tilt angle around the pitch axis of the upper leg relative to the vertical direction. That is, the tilt angle decreases monotonically as the hip height rises. Consequently, an inclination sensor that measures the tilt angle around the pitch axis of the upper leg relative to the vertical direction can also be used as a sensor to measure (estimate) the hip height. In that case, the controller 30 sets the target angle to the standing position angle corresponding to the standing position of the user, and raises the upper limit of the torque limiter as the tilt angle of the upper leg decreases. Furthermore, as described above, "the tilt angle of the upper leg", expressed in more detail, is equivalent to the tilt angle around the pitch axis of the upper leg relative to the vertical direction.

The leg assist device of the embodiment comprises an electric motor as the actuator. The leg assist device may employ a hydraulic motor, a pneumatic motor, etc. The leg assist device of the embodiment assists the knee joint motion. The leg assist device may comprise an actuator that applies torque to a hip joint and/or an ankle joint.

The controller 30 of the leg assist device realizes a method of assisting standing up that, in summary, includes the following steps.

(1) Measuring the lower leg link angle. This step corresponds to S6 of FIG. 5.
(2) Computing the command torque for the actuator based on the difference between the lower leg link angle and the target angle. This step corresponds to S9 of FIG. 5.
(3) Modifying the command torque to the upper limit torque if the computed command torque is greater than the upper limit torque. This process is included in S9 of FIG. 5.
(4) Outputting the modified command torque to the actuator. This process corresponds to S10 of FIG. 5.

Furthermore, the controller 30 sets the target angle to the standing position angle corresponding to the user's standing position (S4). Further, the controller 30 raises the upper limit of the torque limiter as the hip height of the user rises (S8).

Specific examples of the present invention are described above in detail, but these merely illustrate some possibilities of the teachings and do not restrict the scope of the claims. The art set forth in the claims includes variations and modifications of the specific examples set forth above. Further, the technical elements disclosed in the specification or the drawings have technical utility separately or in all types of combinations, and are not limited to the combinations set forth in the claims at the time of filing of the application. Furthermore, the art disclosed in the specification or the drawings may be utilized to simultaneously achieve a plurality of aims, and has technical utility by achieving any one of these aims.

Reference Signs List

10: leg assist device, 12: controller, 20: upper leg link, 30: controller, 32: feed-back control module, 34: torque limiter, 36 torque adjusting module, 40: knee joint mechanism, 42: motor (actuator), 43: angle sensor, 50: lower leg link, 96: load sensor, 100: user, 110: affected leg, 112: upper leg, 114: knee, 116: lower leg

The invention claimed is:

1. A leg assist device that assists standing up motion of a user, the leg assist device comprising:

an upper leg link to be attached to an upper leg of the user;

a lower leg link to be attached to a lower leg of the user;

a rotary joint that connects the lower leg link to the upper leg link, the rotary joint having an actuator that rotates the lower leg link; and a controller having a feed-back control module that computes a command torque for the actuator based on a difference between a lower leg link angle and a target angle, the controller controls the actuator so that the lower leg link angle matches the target angle;

wherein:

the controller has a torque limiter that limits magnitude of the command torque computed by the feed-back control module;

the controller sets the target angle to a standing position angle corresponding to a user's standing position; and the controller raises an upper limit of the torque limiter as a user's hip height rises.

2. The leg assist device of claim 1, wherein the controller changes the target angle to a seated position angle corresponding to a user's seated position when the user's hip height does not reach a predetermined threshold height within a predetermined time period from starting the standing up assist control.

3. The leg assist device of claim 1, wherein the controller raises the upper limit of the torque limiter when the user's hip height does not reach a predetermined threshold height within a predetermined time period from starting the standing up assist control.

4. The leg assist device of claim 2, wherein the controller vibrates the lower leg link before changing the target angle to the seated position angle.

* * * * *